US006845846B1

United States Patent
Gragnano

(10) Patent No.: US 6,845,846 B1
(45) Date of Patent: Jan. 25, 2005

(54) CLIMBING AID

(76) Inventor: Anthony Gragnano, 2624 Bartholomew Dr., Vineland, NJ (US) 08361

( * ) Notice: Subject to any disclaimer, the term of this patent is extended or adjusted under 35 U.S.C. 154(b) by 0 days.

(21) Appl. No.: 10/756,077

(22) Filed: Jan. 13, 2004

(51) Int. Cl.$^7$ .............................................. A63B 27/00
(52) U.S. Cl. ....................................... 182/134; 182/221
(58) Field of Search ................................ 182/221, 134, 182/135, 136, 133, 3, 189; 36/62, 113, 66, 136, 7.1 R; 248/216.1, 217.3, 218.4

(56) References Cited

U.S. PATENT DOCUMENTS

| 2,835,426 A | 5/1958 | Terry |
| 3,640,358 A | 2/1972 | Smith |
| 4,153,139 A * | 5/1979 | Houch .......................... 182/221 |
| 4,530,420 A | 7/1985 | Hobbs |
| 4,730,702 A | 3/1988 | Torbett |
| 4,938,313 A | 7/1990 | Rullo et al. |
| 4,989,693 A | 2/1991 | Williams |
| 4,993,515 A | 2/1991 | Green et al. |
| 5,080,194 A | 1/1992 | Williams |
| 5,231,775 A | 8/1993 | Trent, Jr. |
| 5,853,067 A | 12/1998 | Cutler |
| 6,148,959 A | 11/2000 | Shay |
| 6,405,832 B1 * | 6/2002 | Willis .......................... 182/221 |
| 6,578,668 B2 * | 6/2003 | Haltom ........................ 182/221 |

* cited by examiner

Primary Examiner—Hugh B. Thompson, II
(74) Attorney, Agent, or Firm—Norman E. Lehrer

(57) ABSTRACT

A climbing aid including an elongated member with a first end and a second end, a generally rigid pad member secured to the first end of the shank, and a stirrup and spike attached adjacent the second end of the shank is disclosed. The pad member is secured to a metal support. An adjustable strap secures the pad and the support to the wearer's leg. The shank is pivotally mounted to the support of the pad via a housing and a pivot member that fits within the housing. The shank may pivot laterally or transversely. The housing prevents the pad and support from twisting the pad about the wearer's leg as the wearer climbs or stands on a pole. The length of the shank may also be adjusted. A strap extends from the stirrup and around a part of the shank and secures the wearer's foot to the stirrup.

5 Claims, 2 Drawing Sheets

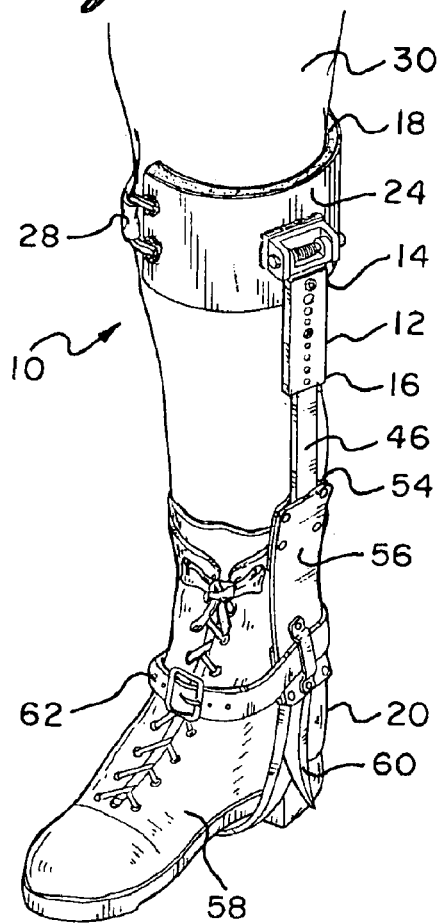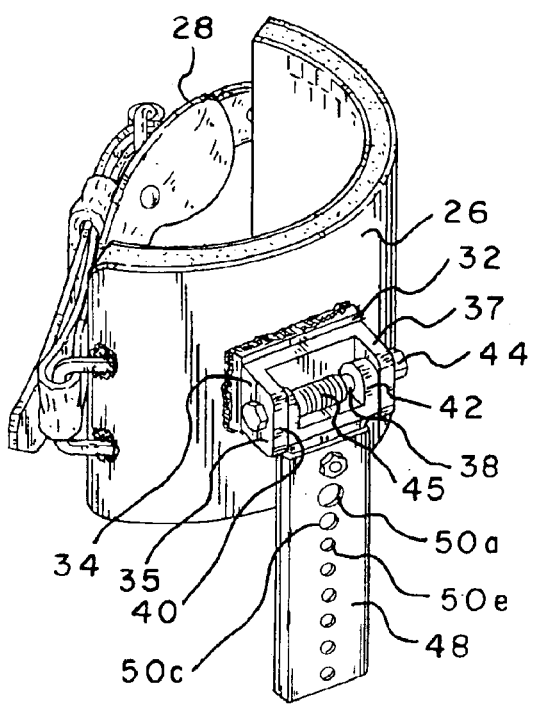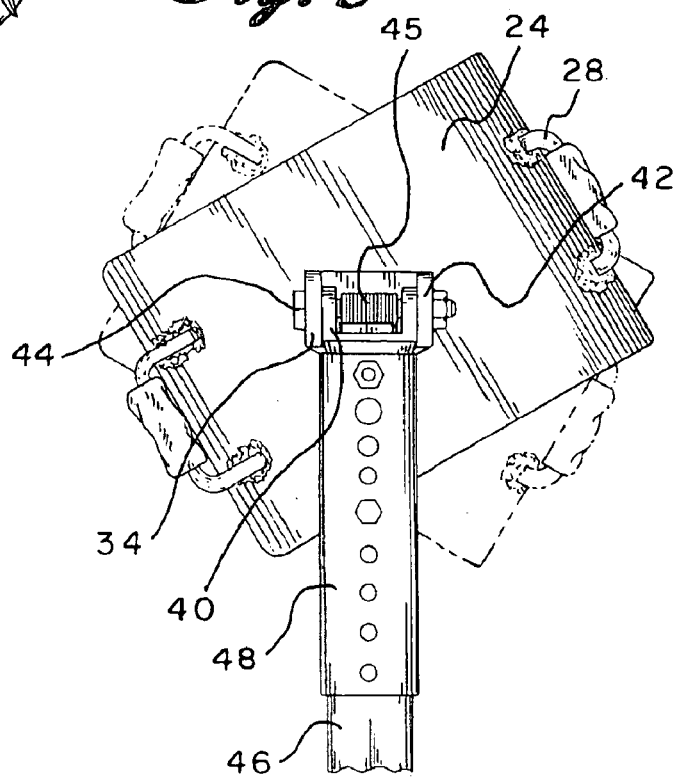

CLIMBING AID

BACKGROUND OF THE INVENTION

The present invention is directed toward a climbing aid and more particularly, toward a device that is worn on a person's leg and foot in order to aid the person to climb a wooden structure such as a pole or a tree.

Climbing aids are often used by tree climbers and electrical, phone, or cable company personnel. These aids assist a person to climb a tree, pole, or the like in order to trim a tree limb or maintain or repair electrical cables or such. Typically such devices include a shank with a telescoping sleeve located at one end adapted to be attached to a pad that fits around the shin of the wearer and a stirrup located at the opposite end of the shank upon which the wearer's foot rests during use. A spike or gaff projects outwardly from the shank adjacent the stirrup end of the shank and penetrates into the tree or pole. A strap connects to the shank by a split ring and extends from the stirrup and around a part of the shank and secures the wearer's foot to the stirrup. An additional strap fits through a metal loop welded to the sleeve to secure the sleeve to the wearer's shin.

A typical example of such an aid is disclosed in U.S. Pat. No. 5,853,067 to Cutler. Cutler discloses a climbing apparatus that includes an elongated shank and a stirrup attached to an end of the shank. The stirrup is engageable with the footwear of the user. The apparatus also includes a leg support attached to an opposite end of the shank and is engageable with the leg of the user. A spike is attached to either the stirrup or the shank to provide support during climbing.

U.S. Pat. No. 4,530,420 to Hobbs also discloses a climbing apparatus that includes an inflexible socket member connected to a foam pad which receives the shank portion of a tree climber. The socket member is formed so that the shank of the tree climber can rotate axially; can pivot forwardly and rearwardly in a plane at right angles to the stirrup of the climber; and can pivot outwardly from the leg of the climber.

Neither of the devices disclosed in the patents discussed above, however, prevents the wearer's discomfort or pain that is typically associated with the climbing aids. Specifically, opposing forces are at work while the wearer climbs the pole. That is, as the spike digs into the pole, the pad has a tendency to twist about the wearer's leg. The shank typically presses against the wearer's leg and is also forced backward, behind the knee. These actions cause the climbing aid to become unstable and also may cause the wearer pain, injury, or discomfort as he or she attempts to climb or to work while on the pole.

Therefore, a need exists for a climbing aid that provides stability and comfort to the wearer as he or she climbs a pole.

SUMMARY OF THE INVENTION

The present invention is designed to overcome the deficiencies of the prior art discussed above. It is an object of the present invention to provide an aid to help a person climb a tree, pole, or the like.

It is another object of the present invention to provide an adjustable climbing aid.

It is a further object of the present invention to provide a climbing aid that protects the wearer's leg while climbing.

In accordance with the illustrative embodiments demonstrating features and advantages of the present invention, there is provided an elongated, generally vertically extending member or shank with a first end and a second end, a generally rigid pad member secured to the first end of the shank, and a stirrup secured or otherwise attached adjacent the second end of the shank. The pad member is secured to a metal support. The pad member has an adjustable strap to secure the pad member and the support to the wearer's leg. The shank is pivotally mounted to the metal support of the pad member via a housing and a pivot member that fits within the housing. The shank may pivot laterally or transversely. The housing, however, prevents axial movement of the pad member and metal support or otherwise prevents the pad member and support from twisting about the wearer's leg. Through the use of a telescoping sleeve, the length of the shank may also be adjusted. Furthermore, a strap extends from the stirrup and around a part of the shank and secures the wearer's foot to the stirrup. A spike extends outwardly from the shank and grips the pole while the wearer climbs the pole.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 1 is a front perspective view of the climbing aid of the present invention being worn by a person;

FIG. 2 is a front perspective view of the top portion of the climbing aid of the present invention;

FIG. 3 is a side view of the top portion of the climbing aid of the present invention illustrating the partial front to back range of motion of the pad and support relative to the shank;

DETAILED DESCRIPTION OF THE PREFERRED EMBODIMENT

Figure 4:
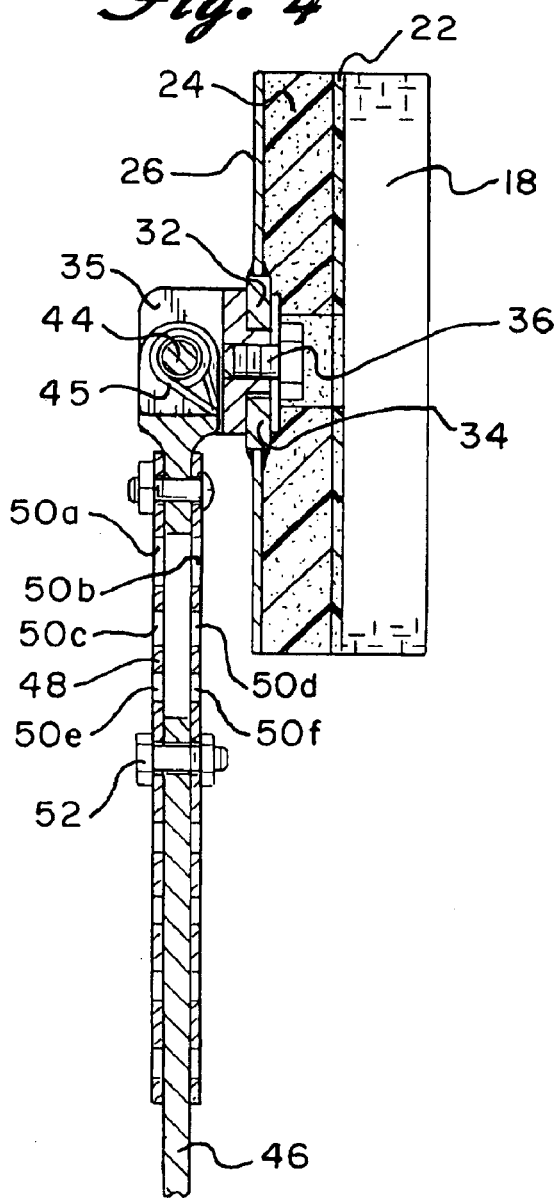
FIG. 4 is a cross-sectional view of the climbing aid of the present invention.

Referring now to the drawings in detail wherein like reference numerals have been used throughout the various figures to designate like elements, there is shown in FIG. 1 a climbing aid constructed in accordance with the principles of the present invention and designated generally as 10.

It should be realized that while only a right leg climbing aid will be described, the present invention includes a climbing aid for a right leg and a left leg. Thus, it will be understood that the left leg climbing aid will be the mirror image of the right leg device 10 being described.

The climbing aid 10 of the present invention essentially includes an elongated, generally vertically extending member or shank 12 with a first or top end 14 and a second or lower end 16, a generally rigid pad member 18 secured to the first end 14 of the shank 12, and a stirrup 20 secured or otherwise attached adjacent the second end 16 of the shank 12.

The pad member 18 is secured to the inner side 22 of a metal support 24. The shank 12 is secured to the outer side 26 of the metal support 24 as will be described in greater detail below. The pad member 18 and support 24 are curved so as to be adapted to be secured around the wearer's shin and calf. The pad member 18 has an adjustable strap 28 to secure the pad member 18 and support 24 to the wearer's leg 30. (See FIG. 2.) The pad member 18 may be made from rubber, foam or similar material and should be thick enough to act as a shock absorber. The pad member 18 and support 24 are molded so that they covers a majority of the shin portion of the wearer's leg 30. That is, the pad member 18 and support 24 should cover the front, inside, and back of the wearer's leg. (See FIG. 1.)

Figure 5:
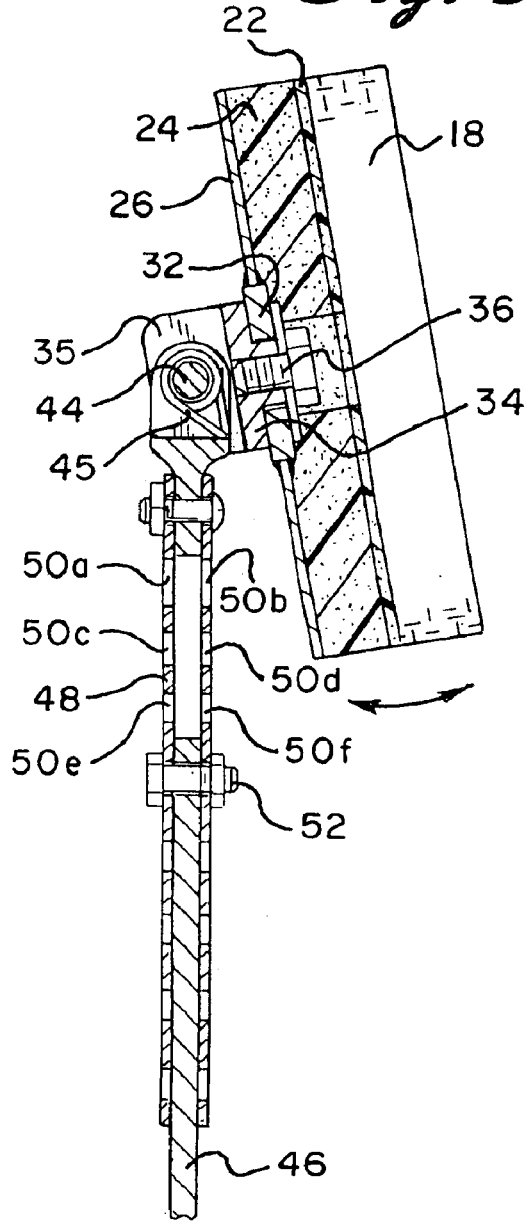
FIG. 5 is a cross-sectional view of the climbing device of the present invention illustrating the partial inward and outward pivotal motion of the pad and support relative to the shank.

The shank 12 is pivotally mounted to the metal support 24 of the pad member 18. That is, a metal plate 32 is secured to the outer side 26 of the metal support 24. A metal housing member 34 with apertured ears 35 and 37 is pivotally mounted to the plate 32 via fastening means, such as bolt 36 so as to be rotatable about the horizontal axis of the bolt 36. (See FIGS. 3 and 5.) The first end 14 of the shank 12 has a pivot member 38 secured thereto. The pivot member 38 may be generally U-shaped with ears 40 and 42 that are in alignment with the ears 35 and 37 of the housing member 34. Each arm 40 and 42 has a hole formed therethrough. A bolt 44, or similar fastening means, passes through the holes of the ears 40 and 42 and the corresponding aperatures in the ears 35 and 37 of the housing member 34 and secures the shank 12 to the housing member 34. (See FIG. 2.) As shown most clearly in FIG. 5, a torsion coil spring 45 surrounding the bolt 44 biases the bottom of the pad member 18 away from the shank 12.

As a result of the arrangement just described, the pad member 18 can rotate relative to the shank 12 about the horizontal axis defined by the axis of the bolt 36. Furthermore, the pad member 18 can pivot somewhat relative to the shank 12 about the horizontal axis defined by the axis of the bolt 44. As can be seen, the horizontal axis defined by the bolt 36 is perpendicular or orthogonal to the horizontal axis defined by the bolt 44. Furthermore, and as pointed out above, the pad member 18 is biased away from the shank by the spring 45. However, the joint between the pad member 18 and the shank 12 prevents the pad member from any rotating or pivoting motion around the vertical axis defined by the shank 12. While this arrangement allows for some desirable limited movement of the pad member 18, it prevents the type of rotational movement that causes chafing or cutting or other discomfort to a person using the climbing aid.

So as to permit the climbing aid 10 to be fitted to different users, the length of the shank 12 may be adjusted. Accordingly, the shank 12 is made so as to telescope and includes an inner member 46 and an outer member 48. The outer member 48 is hollow so that the inner member 46 may be slidably mounted therein. (See FIG. 4.) Located along the length of both sides of the outer member 48 of the shank 12 is a plurality of apertures 50a–50f. The apertures allow for adjusting the length of the shank 12. That is, the inner member 46 also has a plurality of apertures located along the length thereof. An aperture of the inner member may be aligned with an aperture located on the outer member as desired. A bolt 52 or similar fastening means may be used to secure the inner member to the outer member at the desired apertures. While one type of means for adjusting the length of the shank is described, it should be realized that any type of adjusting means known in the art may be used. In this manner the length of the shank may be adjusted as desired by the wearer.

The stirrup 20 is secured to the inner member 46 of the shank 12. That is, the end 54 of the inner member 46 of the shaft 12 opposite the end of the inner member 46 that extends within the outer member 48 of the shank 12 has a sleeve 56 attached thereto. The sleeve 56 is attached to the stirrup 20. The wearer's foot 58 rests within the stirrup 20 during use. (See FIG. 1.) A spike or gaff 60 is attached to the sleeve 56 and projects outwardly from the shank 12 adjacent the stirrup end of the shank and penetrates the tree or pole when the wearer is climbing. An adjustable strap 62 extends from the stirrup 20 and a part of the shank 12 and secures the wearer's foot 58 to the stirrup 20.

The present invention provides an improved climbing aid that protects the wearer's legs while he or she is climbing a pole, tree, or the like. The climbing aid of the present invention also allows the climber to climb safely and to stand comfortably while working from the pole.

The present invention may be embodied in other specific forms without departing from the spirit or essential attributes thereof and accordingly, reference should be made to the appended claims rather than to the foregoing specification as indicating the scope of the invention.

I claim:

1. A climbing aid worn by a person while climbing a wooden structure comprising:

an elongated member with a first end and a second end, said elongated member defining a substantially vertical axis;

a pad member and a rigid support attached thereto;

a stirrup attached adjacent said second end of said elongated member;

a spike attached to said stirrup; and means for pivotally mounting said first end of said elongated member to said support, said mounting means adapted to allow said elongated member to pivot about two orthogonal horizontal axes relative to said pad member while preventing rotation of said pad member about said vertical axis.

2. The climbing aid of claim 1 wherein said mounting means including a plate secured to said support and a housing member secured to said plate, said first end of said elongated member having a pivot member that is secured to said housing member.

3. The climbing aid of claim 2 wherein said pivot member is generally U-shaped with two arms with means for fastening said pivot member to said housing member.

4. The climbing aid of claim 3 wherein said fastening means is a bolt.

5. The climbing aid of claim 2 wherein said support and said plate are metal.

* * * * *